United States Patent
Duong et al.

(10) Patent No.: US 9,439,709 B2
(45) Date of Patent: Sep. 13, 2016

(54) CRYOABLATION BALLOON CATHETER WITH GUIDE WIRE LUMEN

(71) Applicant: Horizon Scientific Corp., Irvine, CA (US)

(72) Inventors: Thach Buu Duong, Tustin, CA (US); Min Frank Zeng, Irvine, CA (US)

(73) Assignee: Cryofocus Medtech (Shanghai) Co., Ltd. (CN)

( * ) Notice: Subject to any disclaimer, the term of this patent is extended or adjusted under 35 U.S.C. 154(b) by 192 days.

(21) Appl. No.: 14/170,267

(22) Filed: Jan. 31, 2014

(65) Prior Publication Data

US 2015/0216581 A1    Aug. 6, 2015

(51) Int. Cl.
*A61B 18/02*    (2006.01)

(52) U.S. Cl.
CPC ........ *A61B 18/02* (2013.01); *A61B 2018/0212* (2013.01); *A61B 2018/0262* (2013.01)

(58) Field of Classification Search
CPC .......... A61B 18/02; A61B 2018/0212; A61B 2018/262
See application file for complete search history.

(56) References Cited

U.S. PATENT DOCUMENTS

| | | | | |
|---|---|---|---|---|
| 5,334,181 A | * | 8/1994 | Rubinsky | A61B 18/02 606/20 |
| 5,501,681 A | * | 3/1996 | Neuwirth | A61B 18/08 606/21 |
| 5,558,644 A | * | 9/1996 | Boyd | A61B 17/29 604/102.02 |
| 6,551,309 B1 | * | 4/2003 | LePivert | A61B 18/02 606/20 |
| 2005/0165388 A1 | * | 7/2005 | Bhola | A61B 18/1492 606/14 |
| 2006/0270981 A1 | * | 11/2006 | Capuano | A61B 18/02 604/113 |

* cited by examiner

Primary Examiner — Daniel Fowler
(74) Attorney, Agent, or Firm — Raymond Sun

(57) ABSTRACT

A cryoablation system has a catheter that receives working cryogen, the catheter having a catheter body that has a distal section having a freezing element which delivers the working cryogen to a treatment location, and a balloon enclosing the freezing element. The catheter body includes an outer tube that has two delivery tubes and a guide wire tube positioned inside the outer tube.

16 Claims, 14 Drawing Sheets

CRYOABLATION BALLOON CATHETER WITH GUIDE WIRE LUMEN

BACKGROUND OF THE INVENTION

1. Field of the Invention

The present invention relates to a medical device, and in particular, to a cryoablation catheter for freezing and destroying biological tissues.

2. Description of the Prior Art

Cryosurgical therapy involves the application of extremely low temperature and the use of complex systems designed to suitably freeze the target biological tissue to be treated. Many of these systems use cryoprobes with particular shapes and sizes that are designed to contact a selected portion of the tissue without undesirably impacting adjacent healthy tissues or organs. Extreme freezing is produced with refrigerants that are introduced through a flexible or rigid probe. The freezing is then applied to the target tissue through a thermal transfer element formed as a part of the probe and limited to applying the freezing to a relatively small location.

SUMMARY OF THE DISCLOSURE

It is an object of the present invention to provide an improved cryoablation catheter for freezing and destroying biological tissues.

In order to accomplish the objects of the present invention, the present invention provides a cryoablation system having a catheter that receives working cryogen, the catheter having a catheter body that has a distal section having a freezing element which delivers the working cryogen to a treatment location, and a balloon enclosing the freezing element. In one embodiment, the catheter body has an outer tube, a first lumen positioned inside the outer tube and coaxially spaced from the outer tube to define a fluid delivery space, the first lumen having two delivery tubes and a guide wire tube positioned inside the first lumen. In another embodiment, the catheter body has an outer tube, with two delivery tubes, a guide wire tube, and a fluid delivery tube positioned inside the outer tube.

DETAILED DESCRIPTION OF THE PREFERRED EMBODIMENTS

Figure 1:
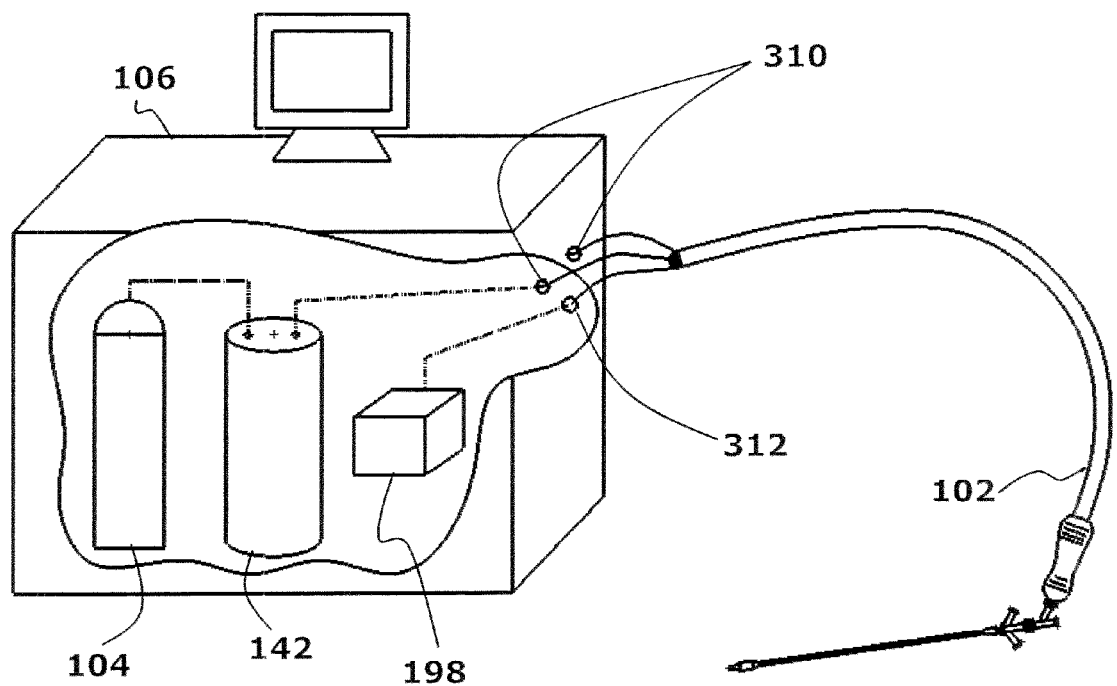
FIG. 1 illustrates a cryoablation catheter system according to the present invention.
Figure 2:
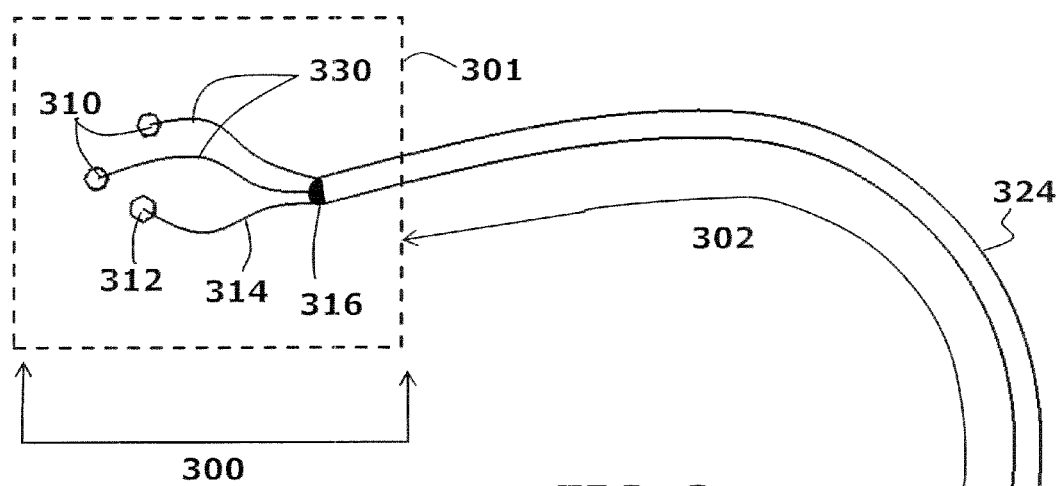
FIG. 2 illustrates the tubing and catheter portions the system of FIG. 1.
Figure 2:
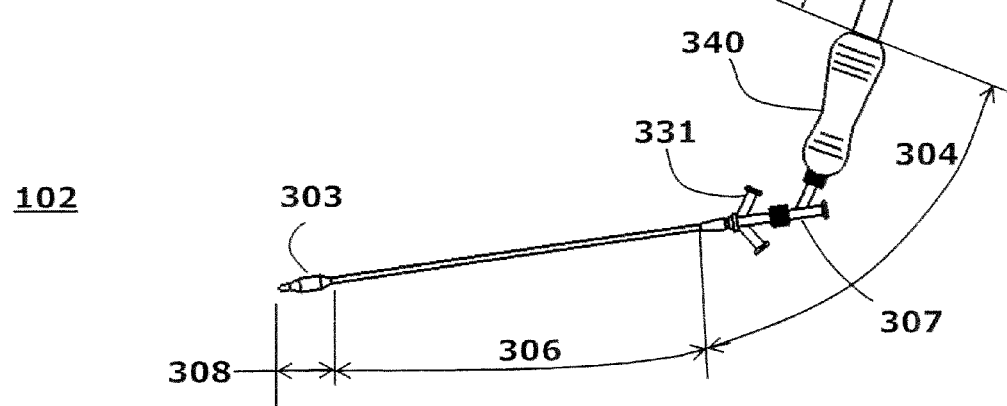

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention is directed to a cryoablation catheter and its construction. In particular, the present invention is directed to different constructions for a cryoablation catheter that incorporates an over-the-wire guide wire tube or lumen. These cryoablation catheters are design to work with a typical cryoablation system 106. The cryoablation system 106 includes a gas source 104, a liquid generator 142, and a vacuum system 198, among other components.

The gas source 104 can be an integral subassembly within a typical cryoablation system 106 or a standalone system that delivers working fluid to the cryoablation system. The gas source 104 includes a high-pressure gas tank, a pressure regulator, and a connecting hose for transporting the gas. A liquid generator 142 is an integral subassembly of the cryoabiation system. It receives working gas from the gas source 104 and converts the gas into liquid cryogen. The liquid generator 142 includes a liquid dewar (which stores cryogenic refrigerant), and heat exchanger(s). The vacuum system 198 is a standalone subassembly that can also be integrated within the cryoablation system 106. The vacuum system 198 serves to provide vacuum insulation to the vacuum chamber 320 where the cryogenic delivery lines are positioned. The vacuum system 198 includes a vacuum pump(s), a vacuum pressure sensor, an on/off electrically-controlled valve, and a connecting hose.

Referring to FIG. 1-16, the cryoablation catheter system of the present invention has a catheter 102 which has a connector section 300, a hose section 302, a proximal section 304, a catheter body 306, and a distal section 308 that functions as an ablation section.

Referring to FIGS. 1-3 and 14-16, the connector section 300 has two interchangeable gas connectors 310 and a vacuum connector 312. The gas connectors 310 receive cold/warm fluid from a typical cryoablation system 106, deliver the fluid from the connector end of the catheter 102 to the distal section 308, and then back to the connector section 300 through a continuous pathway. The continuous pathway is defined by the delivery tubes 330, 332, 4330, 4332, and a double-coiled element 351 incorporated in series with a single-loop element 350 that is located at the distal-most end of the distal section 308. The single-loop element 350 and the double-coiled element 351 are formed using the delivery tubes 330 and 332. The axis of the single-loop element 350 is not concentric, but is perpendicular to the axis of the catheter's outer lumen 328 and the axis of the double-coiled element 351 is concentrically positioned about the centerline of the outer lumen 328. The delivery tubes 330 and 332 are not insulated at the distal section 308 so as to facilitate maximum heat transfer capability.

The vacuum connector 312 is connected to a short vacuum tube 314, which terminates in proximity to an air-tight seal 316 located near the hose section 302. The vacuum tube 314 can be made of stainless steel, copper alloy, or other material such as nylon, FEP (fluorinated ethylene propylene), PTFE™, polyurethane, and polyethylene. The internal opening of the vacuum tube 314 communicates with the catheter vacuum chamber 320 (see FIGS. 7, 8, 9, 11, 13, 15, and 16), which is the chamber or space defined or enclosed by a tube adapter 317, an outer hose 324, a straight connector 345, a three-way connector 307, a four-way connector 331, an outer lumen 328, and among the seven airtight seals 315, 316, 346, 347, 402, 355, and 336 located at the connector section 300, proximal section 304, and the distal section 308, respectively. Even though the connector section 300 is described as having three separate connectors 310 and 312, a single connector assembly 301 can be provided which incorporates and combines all the functional features of the three connectors into one.

Referring to FIGS. 8, 9, 13, 14, 15, and 16, the hose section 302 is constructed with a flexible outer hose 324 made of nylon material or other vacuum-rated tubing materials such as PTFE™, FEP, Pebax™, polyurethane, and polyethylene. At the connector section 300, the hose 324 connects to one end of the tube adapter 317 and forms an airtight seal 315. See FIG. 15. The tube adapter 317 can be made from plastic or metallic material. The tube adapter 317 has a through hole along its length, enabling the delivery tubes 4330 and 4332 and the vacuum tube 314 to pass through. At the second end of the tube adapter 317, an airtight seal 316 is formed among the delivery tubes 4330 and 4332, the vacuum tube 314, and the tube adapter 317. At the proximal section 304, the hose 324 is enclosed within the outer handle 340 and sealed by epoxy to the straight connector 345 that serves as an inner handle piece. The epoxy seal can be replaced by thermally bonding the hose 324 to the straight connector 345, or using EV-cured glue, or a combination thereof. The entire length of the hose 324 encapsulates the two delivery tubes 4330 and 4332 that are positioned parallel to each other inside the hose 324. The delivery tubes 4330 and 4332 can be made of stainless steel, copper alloy, copper-nickel alloy, nylon, FEP, TEFLON™, or polyimide tubes.

Figure 3:
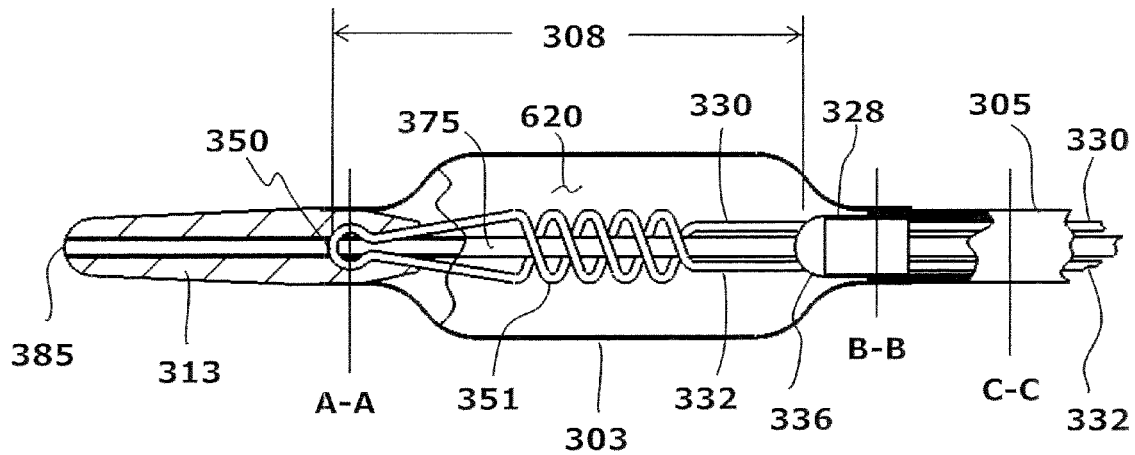
FIG. 3 is a cut-away side view of the distal section of the catheter of FIG. 2.
Figure 4:
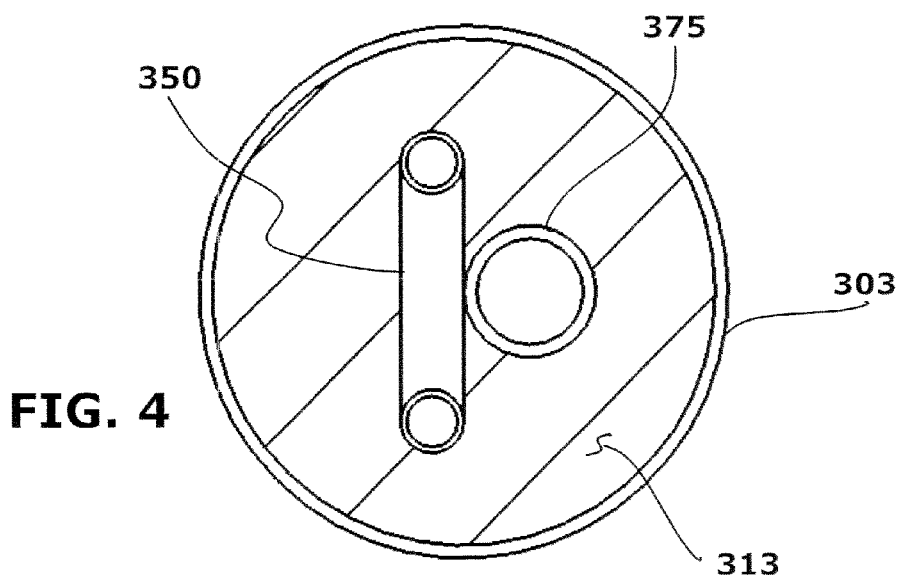
FIG. 4 is a cross-sectional view taken along line A-A in FIG. 3.
Figure 8:
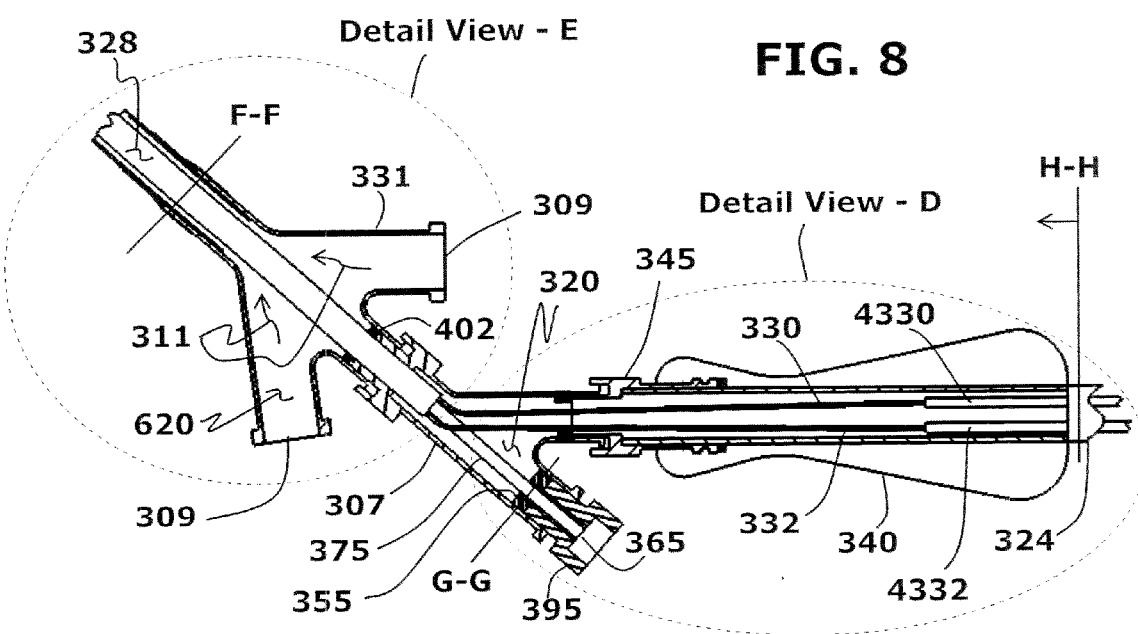
FIG. 8 is a cut-away side view of the proximal section of the catheter of FIG. 2.
Figure 9:
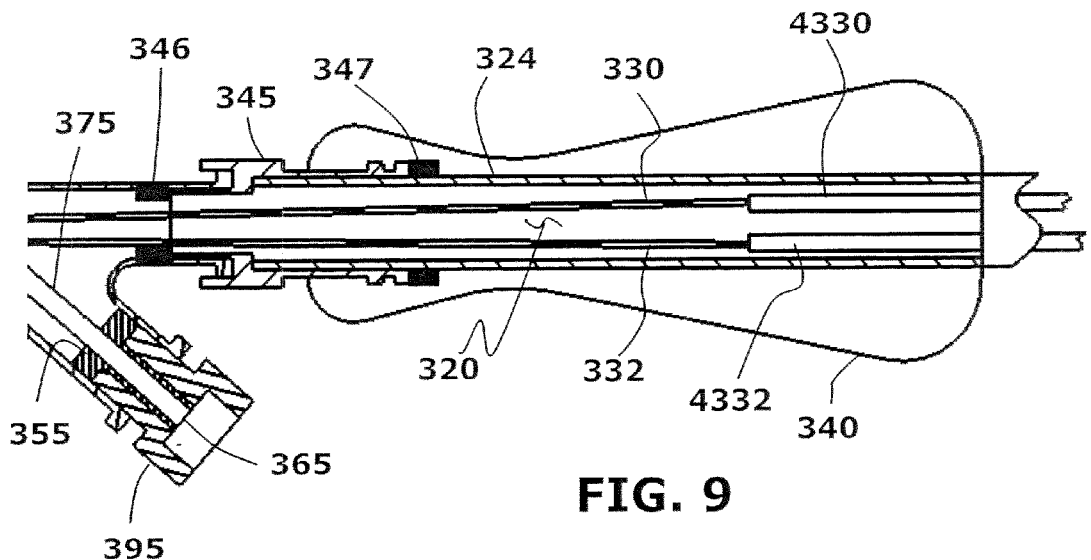
FIG. 9 is an enlarged view of the area D in FIG. 8.

Referring to FIGS. 8-13, the proximal section 304 of the catheter 102 is where the tubes transition internally and externally, and where the flexible outer hose 324 transitions to the outer lumen 328 through three different connectors. Internally within the proximal section 304, the larger-diameter delivery tubes 4330 and 4332 extending from the connector section 300 are joined axially with the two ends of a smaller-diameter delivery tube 330 and 332 within the enclosure of the handle piece 340. The delivery tubes 330 and 332 extend out of the straight connector 345 into a three-way connector 307 that in turn leads into a four-way connector 331 in which an outer lumen 328 is connected. The smaller delivery tubes 330 and 332 enter the inner diameter of the outer lumen 328 at the four-way connector 307 and then exit at other end of the outer lumen 328 into the distal section 308. This is best shown in FIGS. 3 and 8. The delivery tubes 330 and 332 can be made of a stainless steel or copper-nickel alloy. The outer lumen 328 can be a flexible tube made from PEBAX™ material or other flexible material, such as TEFLON™, FEP, nylon, polyetheretherketon (PEEK), polyimide, polyurethane, or polyethylene tubing. The outer lumen 328 can also be made of different durometer hardness along its length, with the lowest durometer section positionED near the distal end. In addition, a layer of tubing positioned coaxially over the outer diameter of the outer lumen 328 can be added to serve different needs. For example, an additional layer can be used to improve thermal insulation. The entire length of the outer lumen 328 encapsulates the two copper-nickel delivery tubes 330 and 332, which are positioned parallel to each other inside the outer lumen 328. The connections between the tubes 330 and 4330, and between 332 and 4332 can be accomplished by a solder/braze material 334 (see FIG. 13).

Figure 6:
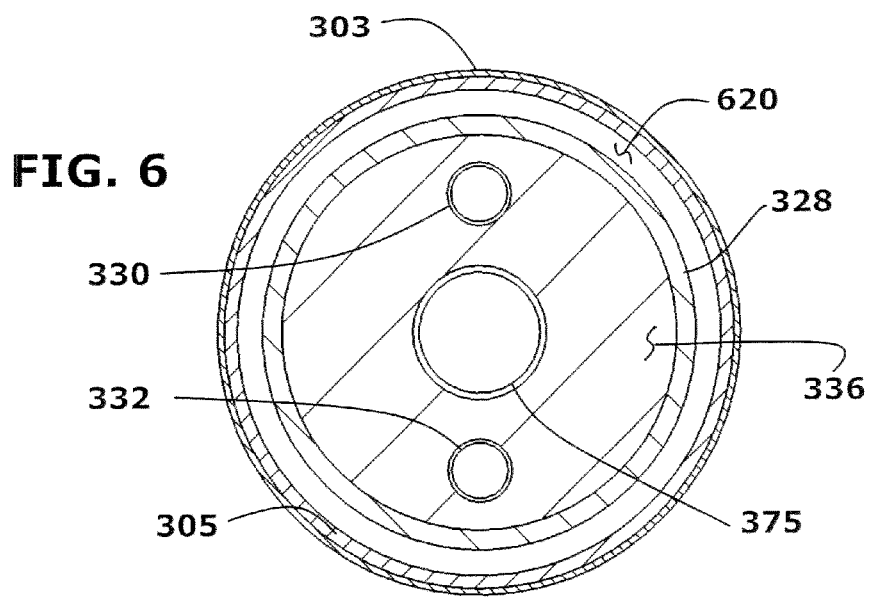
FIG. 6 is a cross-sectional view taken along line B-B in FIG. 3.
Figure 7:
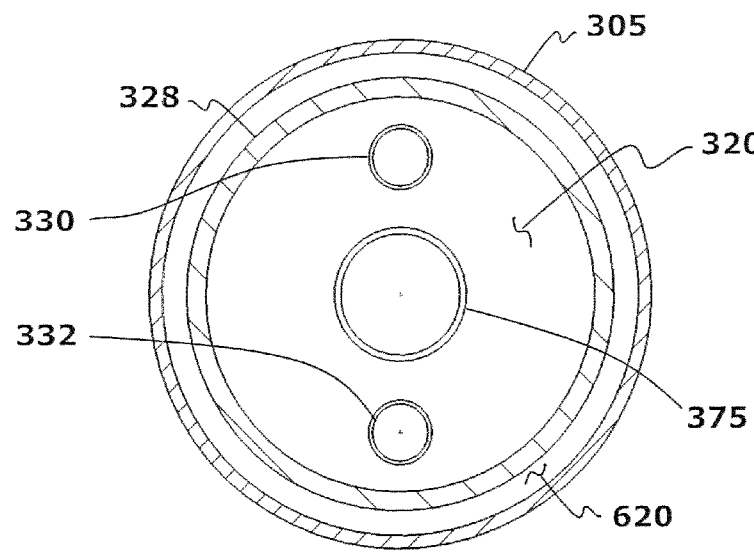
FIG. 7 is a cross-sectional view taken along line C-C in FIG. 3.
Figure 11:
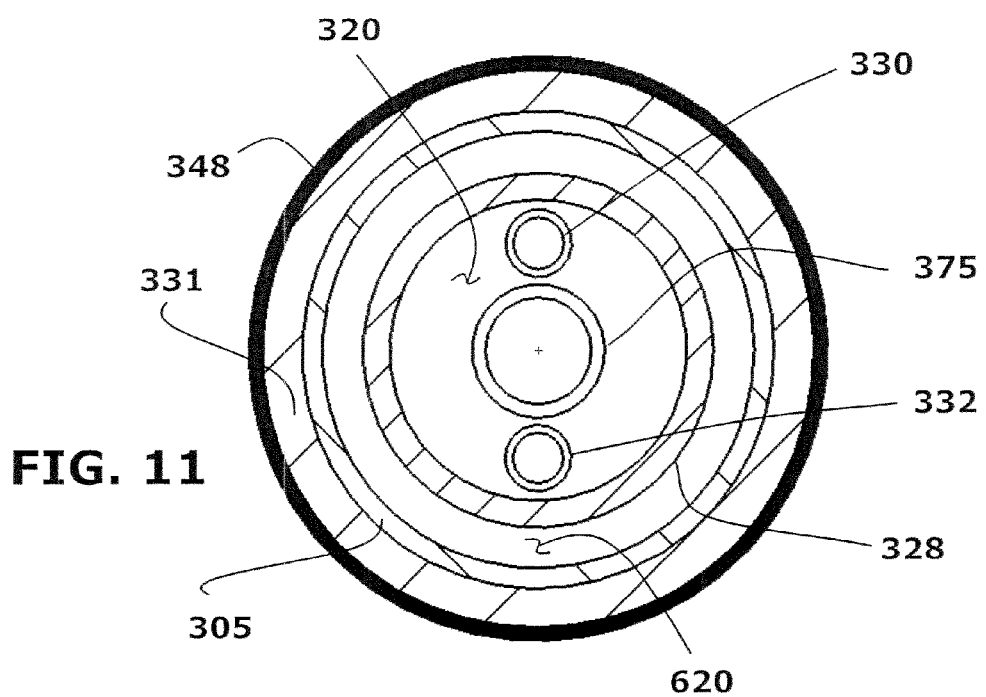
FIG. 11 is a cross-sectional view taken along line F-F in FIG. 8.
Figure 12:
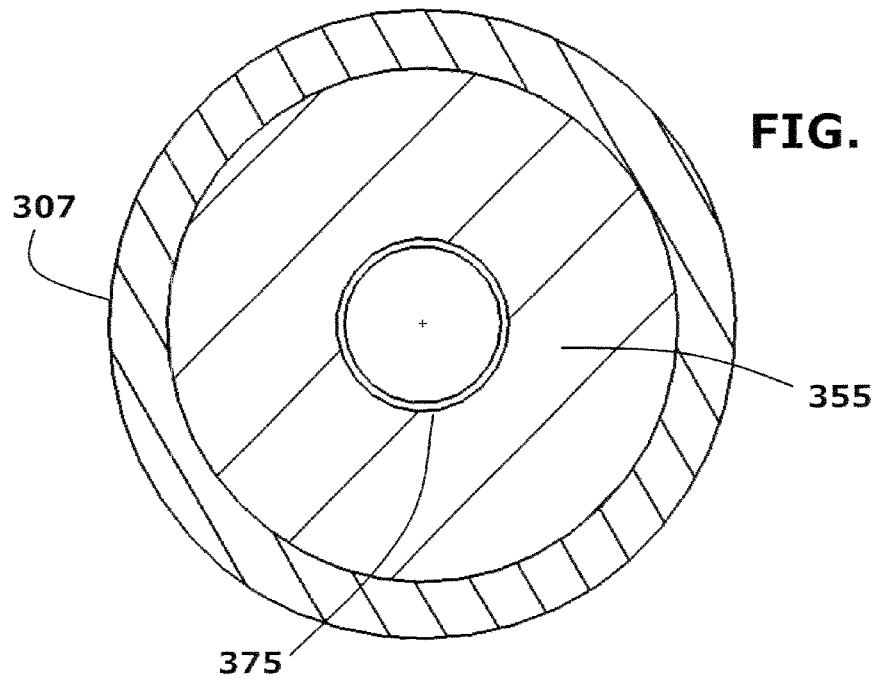
FIG. 12 is a cross-sectional view taken along line G-G in FIG. 8.
Figure 13:
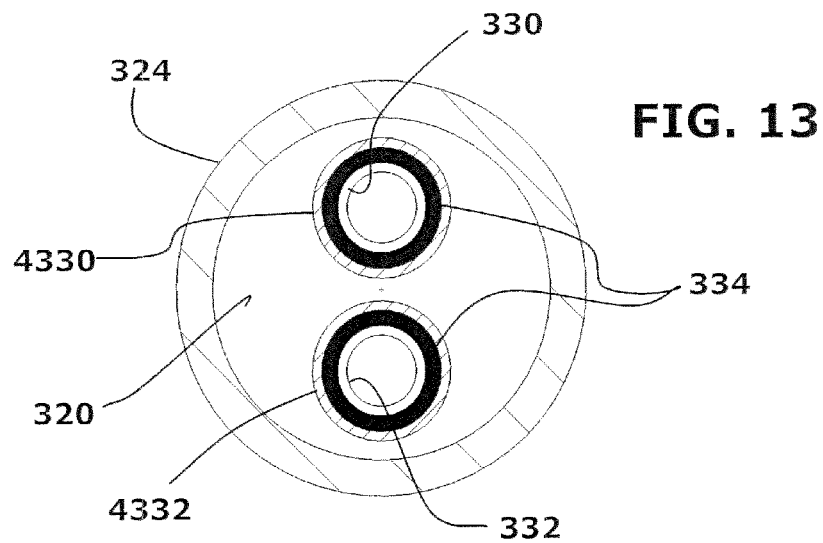
FIG. 13 is a cross-sectional view taken along line H-H in FIG. 8.
Figure 14:
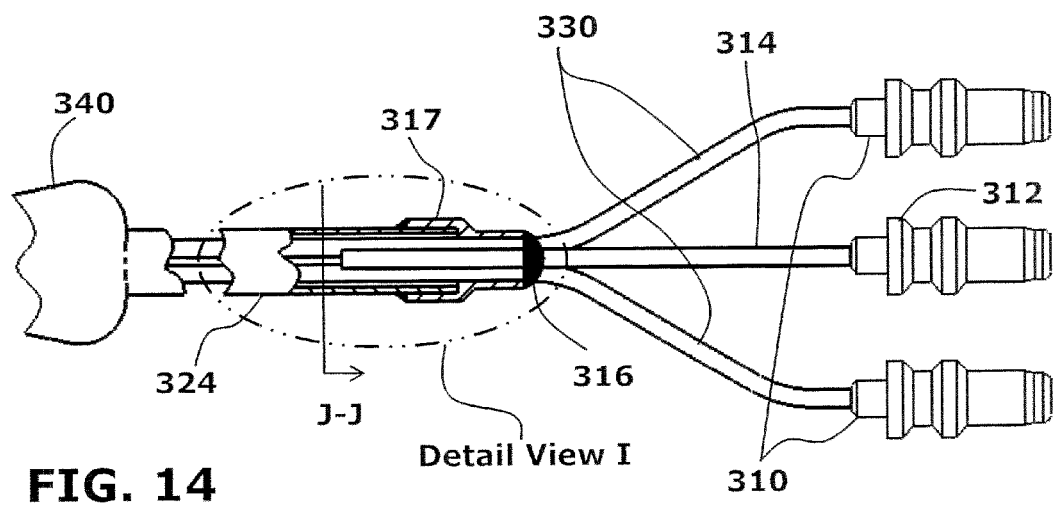
FIG. 14 is a cut-away side view of the connector section of the catheter of FIG. 2.
Figure 15:
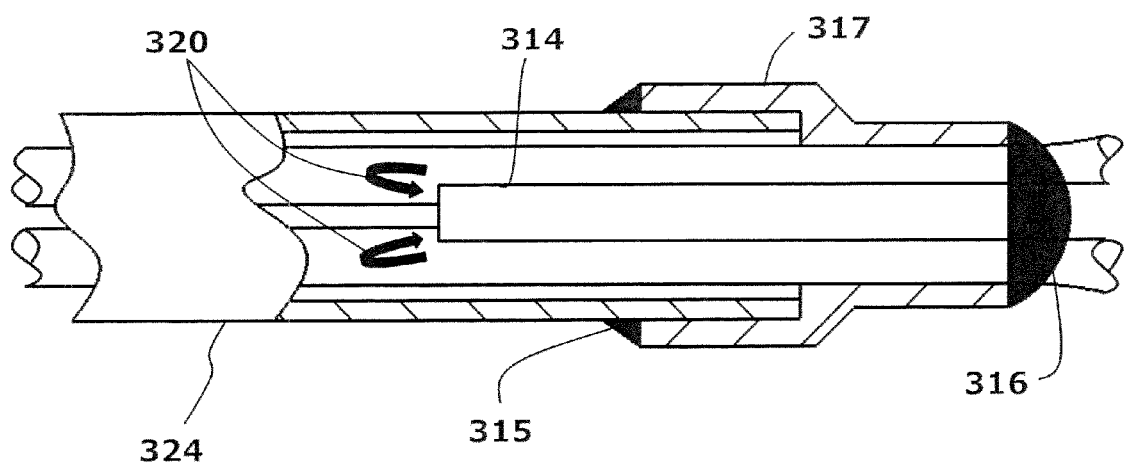
FIG. 15 is an enlarged view of the area I in FIG. 14.
Figure 16:
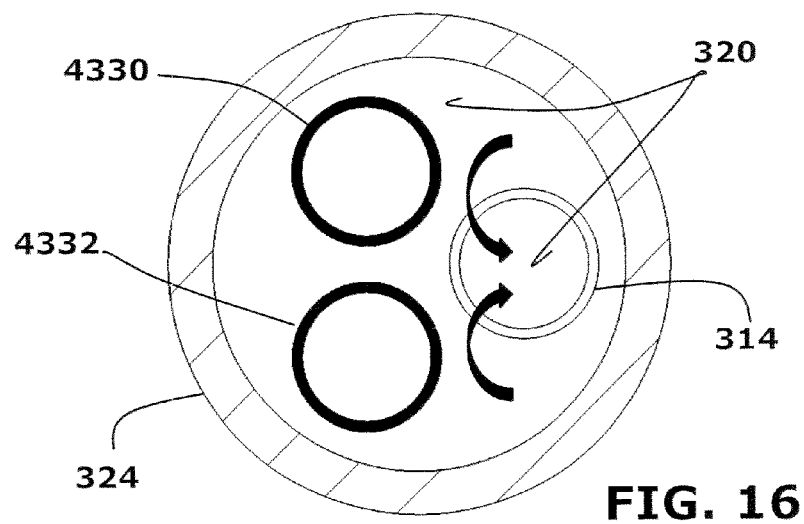
FIG. 16 is a cross-sectional view taken along line J-J in FIG. 14.

As best shown in FIGS. 6, 7 and 11, the catheter body 306 includes two copper-nickel delivery tubes 330, 332 and the guide wire tube 375 positioned parallel within the outer lumen 328 which is enclosed by the balloon-fluid delivery tube 305 positioned concentrically over the outer lumen 328. Thus, the tube 305 essentially defines the catheter body 306 itself and acts as the outer wall of the catheter body 306. The space in between the outer lumen 328 and the balloon-fluid delivery tube 305 serves as the transportation passage and storage area for balloon fluid 311, which is a part of the fluid chamber 620. The combination of material selections, physical sizes (as described below) and mechanical arrangement allows the catheter body 306 to be very flexible. The catheter body 306, along with the distal section 308 described below, is capable of bending around a contour having an angle of less than ninety degrees, and having a bend radius of less than 0.50 inch.

Externally to the proximal section 304, the hose 324 is connected with the straight connector 345 forming an airtight seal 347. The second end of the straight connector 345 connects to one port of the three-way connector 307 forming an air-tight seal 346. The second port of the three way connector 307 houses the guide wire tube 375. An air-tight seal 355 connects the guide wire tube 375 to the guide wire connector 395 and to the second port of the three-way connector 307, creating a guide wire inlet port 365. The guide wire tube 375 is positioned internally within the outer lumen 328 and has a second end that terminates at the distal section 308 where a guide wire outlet port 385 is formed. The third port of the three-way connector 307 connects to the first port of the four-way connector 331 forming an airtight seal 402 between the ports and also with the outer lumen 328. The two side ports of the four-way connector 331 (i.e., the fluid inlet ports 309) receive balloon fluid 311 to fill up the balloon fluid chamber 620. The balloon fluid chamber 620 defines the volume occupied in between the balloon 303, the balloon-fluid delivery tube 305, the four-way connector 331, the outer lumen 328, the flexible soft tip 313, and the airtight seal 402. The fourth port of the four-way connector 331 connects distally to the balloon-fluid delivery tube 305 (see FIGS. 8, 10, & 11) to form a water tight seal.

A strain relief 348 (see FIGS. 10-11) is provided between the balloon fluid delivery tube 305 and the four-way connector 331 at the distal end of the proximal section 304. The strain relief 348 is a flexible plastic or rubber tube or a heat shrink tube, preferably made of nylon, polyurethane, polyethylene, or FEP, which functions to provide strain support to the catheter body 306 by distributing absorbed energy along its length.

The distal section 308 is a non-vacuum insulated section of the catheter 102, and contains a flexible soft tip 313, the guide wire tube 375, a thermal transfer element (i.e., freezing element) defined by the single-loop 350, double-coiled 351, non-insulated sections of the delivery tubes 330, 332, and a balloon 303 that houses the distal section 308. The flexible soft tip 313 is made from a biocompatible low durometer PEBAX™ material having 20% to 35% barium sulfate ($BaSO_4$). The low durometer allows greater tip flexibility, with its softness characteristic preventing unintended physical trauma as the catheter trip travels through the vascular structure. The barium sulfate provides a visual guidance with its radiopaque feature enabling proper catheter placement within the treatment region. The flexible soft tip 313 is heat-bonded to the single-loop element 350 and the guide wire tube 375 forming an airtight bond among them while still allowing the guide wire outlet port 385 to be accessible.

The guide wire tube 375 is a single lumen tube made from low durometer PEBAX™ material. Other materials can also be utilized, such as Polyimide, nylon, FEP, TEFLON™, and polyurethane. At the distal end, the guide wire tube 375 exits the airtight seal 336 and travels through the center of the double-coiled element 351 and to the catheter tip where it is thermally bonded to the single-loop element 350 and the flexible soft tip 313, creating a watertight bond. A guide wire outlet port 385 is formed at the soft tip 313. At the proximal end, the guide wire tube 375 exits the outer lumen 328 into one port of the three-way connector 307. A guide wire connector 395 connects to the guide wire tube 375 and one port of the three-way connector port 307 to form an airtight seal 355 where a guide wire inlet port 365 is formed.

The single-loop element 350 and the double-coiled element 351 can be formed of a flexible material having good fatigue property. The material can be made from annealed 70/30 Copper-Nickel alloy, or stainless steel alloy, with an outer diameter of 0.019 inches (0.508 mm) to 0.026 inches (0.660 mm) and an inner diameter of 0.015 inches (0.406 mm) to 0.020 inches (0.508 mm). The single-loop element 350 and the double-coiled element 351 are designed to be able to slide through circular openings (i.e. the inlet port or opening of a conventional outer guiding catheter) having a diameter that is less than 0.105 inches (2.67 mm) or smaller than 8 French. The compactness as well as the flexibility of the single-loop element 350 and the double-coiled element 351 design enable them to enter the vascular structure easily.

Figure 5:
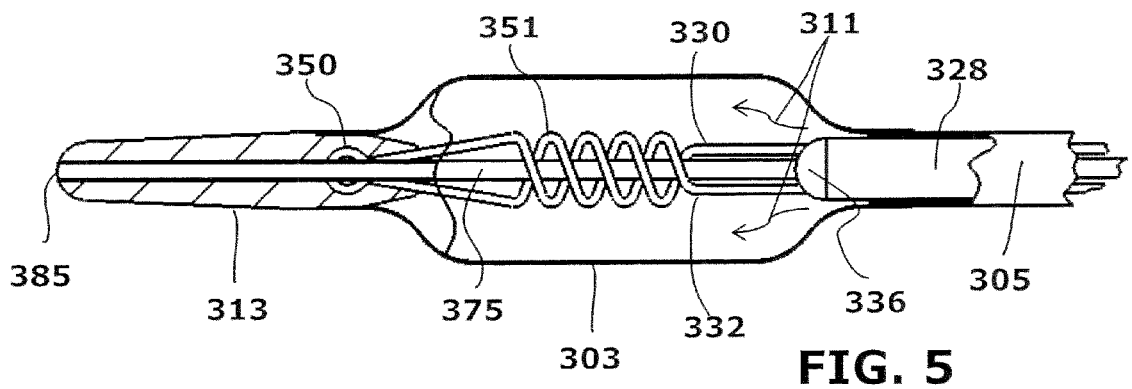
FIG. 5 is the same view as FIG. 3 but with the distal section rotated by one hundred eighty degrees.
Figure 10:
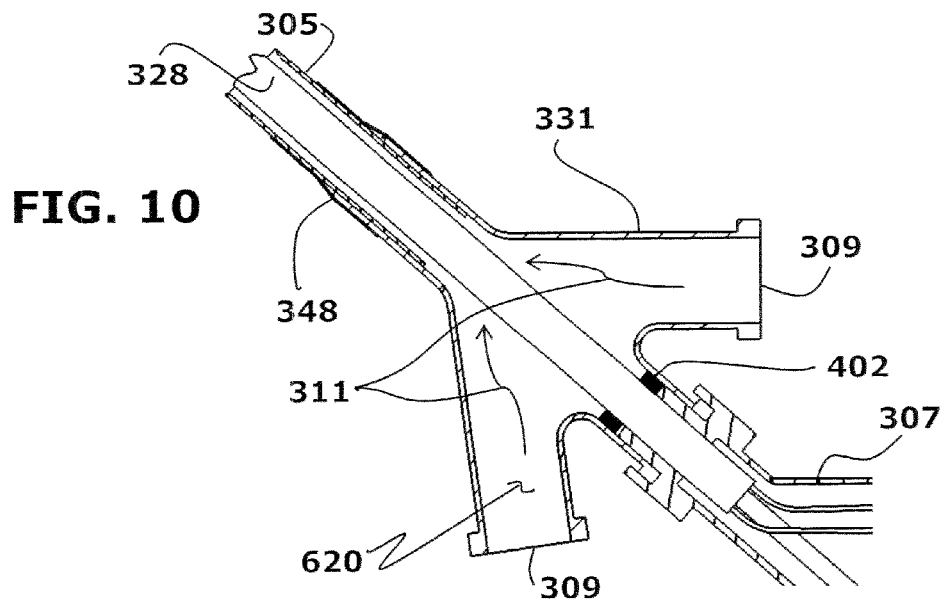
FIG. 10 is an enlarged view of the area E in FIG. 8.

The present invention contains a balloon 303 that encloses most of the distal section 308. The balloon 303 can be made from polyurethane film, nylon, or a PET material, and it extends beyond both sides of the distal section 308, with one (proximal) side forming an airtight seal with a balloon delivery tube 305. The balloon fluid delivery tube 305 is made from a thin-walled and high-strength polyimide, nylon, PET, FEP, Teflon, or PEEK tubing. The balloon fluid delivery tube 305 is covered and positioned concentrically around the catheter outer lumen 328, and carries balloon fluid 311 from the fluid inlet port 309 of the four-way connector 331 as shown in FIGS. 5, 8 and 10. The other (distal) end of the balloon 303 forms an airtight seal with the flexible soft tip 313 (see FIG. 3).

The balloon 303 functions to occlude the flow of blood and to center the distal section 308 within the blood vessel. Blood flow generates a constant heat source and, when directed over the freezing section, will reduce the cold energy being transferred to the treatment area. Heat energy from a high blood flow rate can reach an equilibrium point with the supplied cold energy at the distal section 308 and prevent further ice formation, thereby rendering the treatment ineffective. Therefore, occluding the blood flow allows cold energy to be delivered more effectively, and to concentrate the cold energy at the treatment area, resulting in a more effective energy transfer approach.

The balloon 303 also serves to center the distal section 308 within the blood vessel. Centering of the distal section 308 allows uniform radial cold energy transfer resulting in a concentric treatment zone with the vessel wall. Without this feature, the treatment zone may not be concentric with the vessel wall, thereby possibly over treating one side of the vessel while undertreating the opposite side. Thus, centering the distal section 308 within the vessel wall provides predictable outcomes and a controllable treatment procedure.

Figure 23:
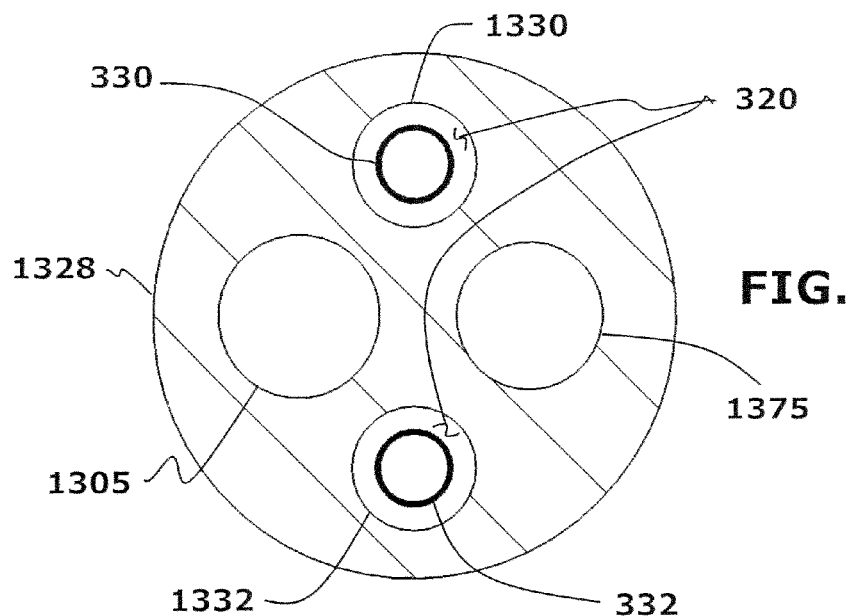
FIG. 23 is a cross-sectional view taken along line M-M in FIG. 19.

FIGS. 19-26 illustrate another embodiment of the catheter 102 according to the present invention. Referring to FIGS. 19-26 (and in particular, FIG. 23), the catheter 102 in this embodiment has a single outer lumen 1328 that has four internal lumens: two delivery tube lumens 1330, 1332, one guide wire lumen 1375, and one balloon fluid delivery lumen 1305. The four internal lumens 1330, 1332, 1376 and 1305 are essentially through-holes that are formed within the singular mass that makes up the single outer lumen 1328. The internal lumens 1330, 1332, 1376 and 1305 are positioned symmetrically about the centerlines of a cross-sectional cut along the length of the single outer lumen 1328. This radial positioning of these internal lumens 1330, 1332, 1376 and 1305 fixes them in place so that they are surrounded and held together by the inner material that makes up the single outer lumen 1328. In essence, the primary difference between this embodiment and the embodiment in FIGS. 3-13 is that the balloon fluid delivery lumen tube 305 in FIG. 7 coaxially encloses the outer lumen 328, whereas the balloon fluid delivery lumen 1305 in FIG. 23 is now a lumen that is positioned inside the outer lumen 1328.

Figure 19:
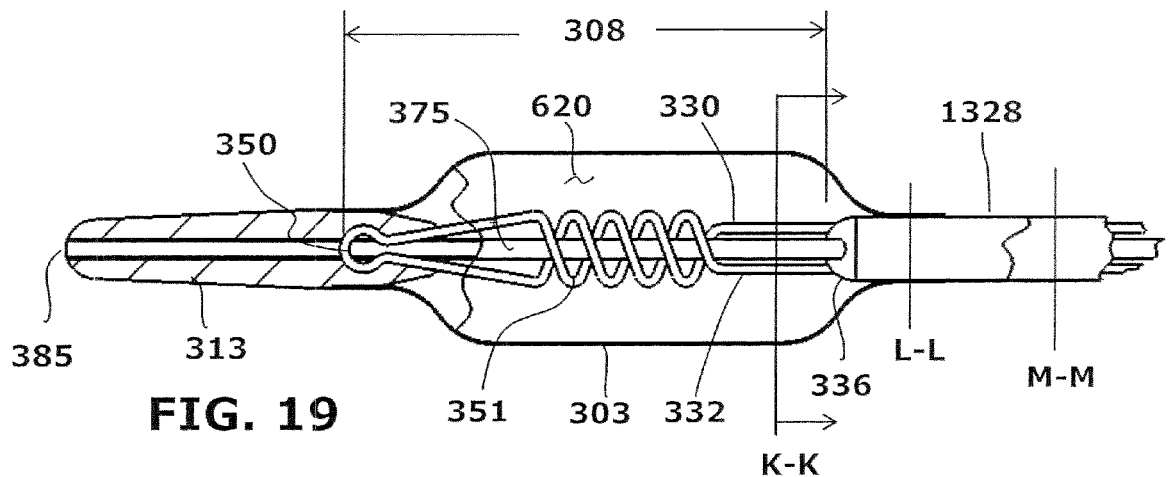
FIG. 19 is a cut-away side view of the distal section of the catheter of FIG. 2 according to another embodiment which has a multi-lumen as an outer lumen.
Figure 20:
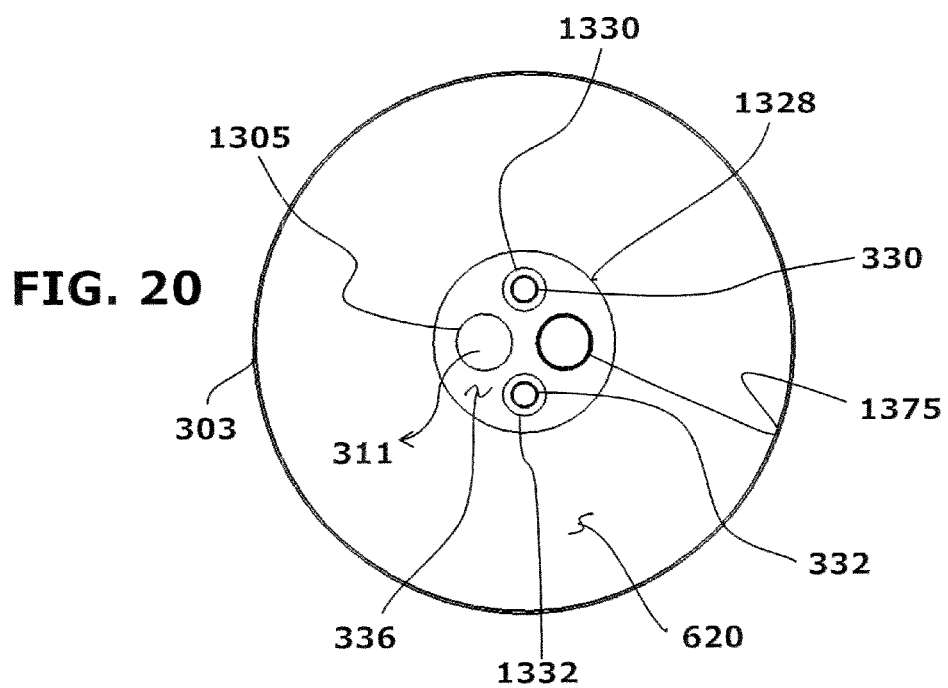
FIG. 20 is a cross-sectional view taken along line K-K in FIG. 19.
Figure 21:
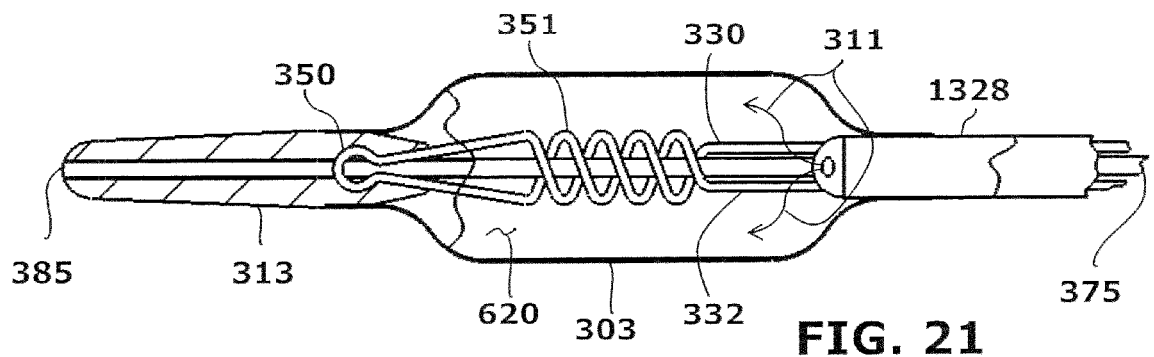
FIG. 21 is the same view as FIG. 19 but with the distal section rotated by one hundred eighty degrees.
Figure 22:
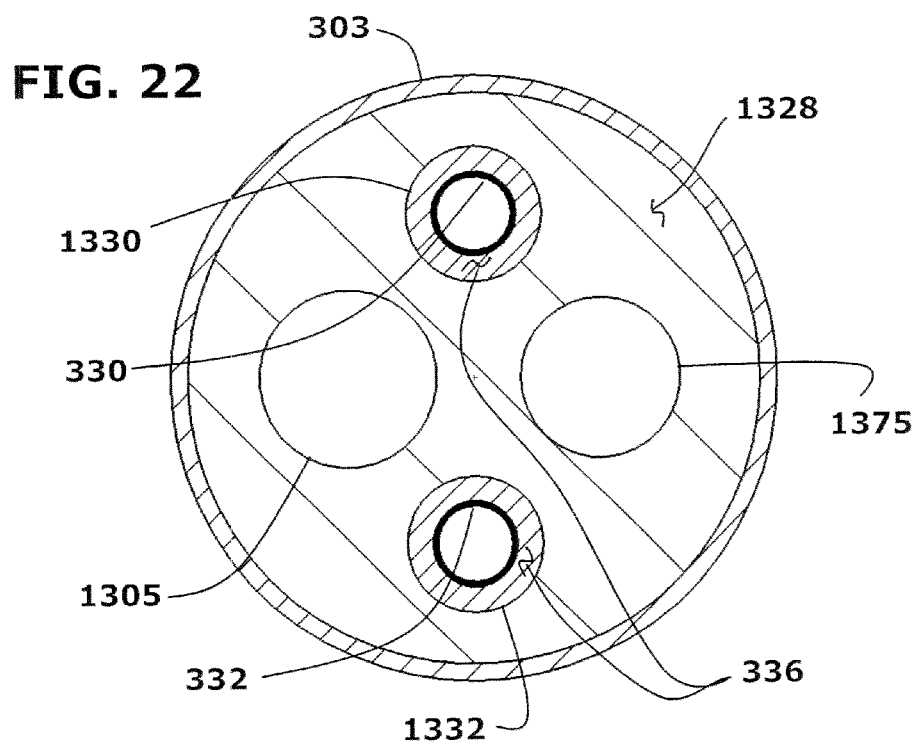
FIG. 22 is a cross-sectional view taken along line L-L in FIG. 19.
Figure 24:
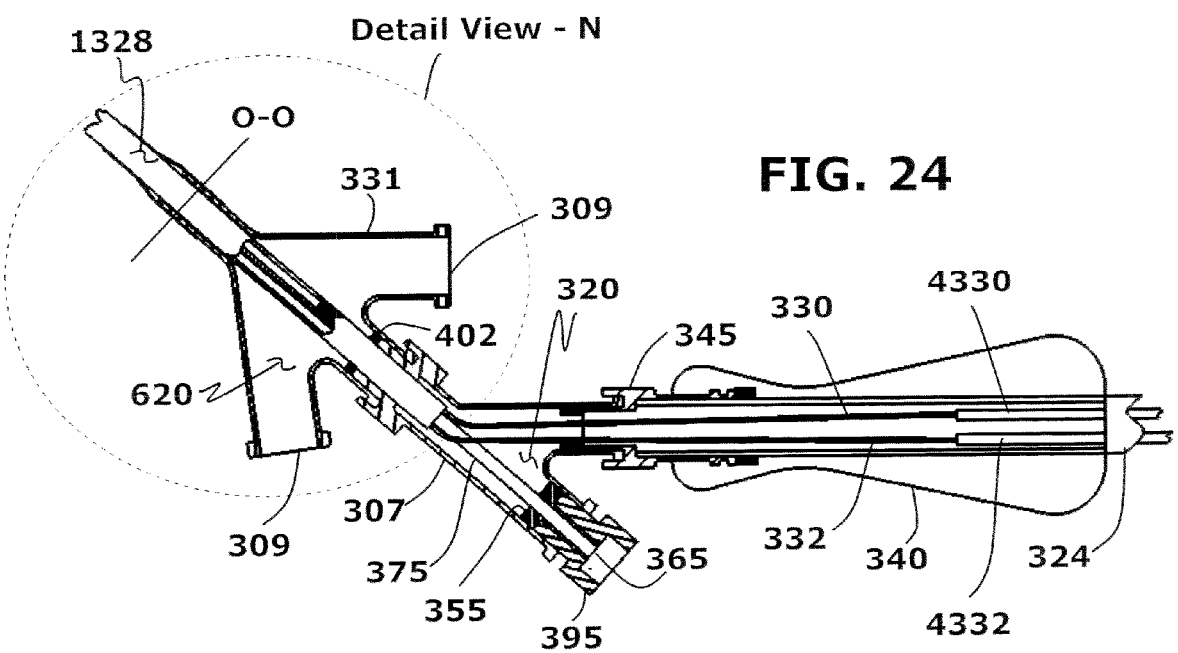
FIG. 24 is a side view of the proximal section of the catheter of FIG. 2 for the embodiment of FIG. 19 that has a multi-lumen as an outer lumen.
Figure 25:
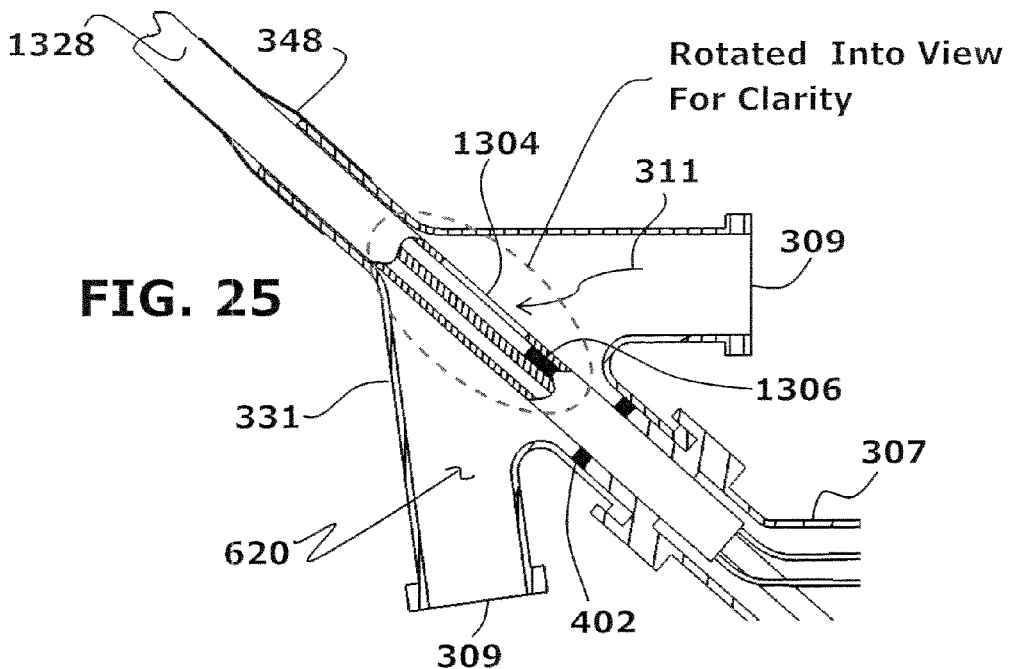
FIG. 25 is an enlarged view of the area N in FIG. 24.
Figure 26:
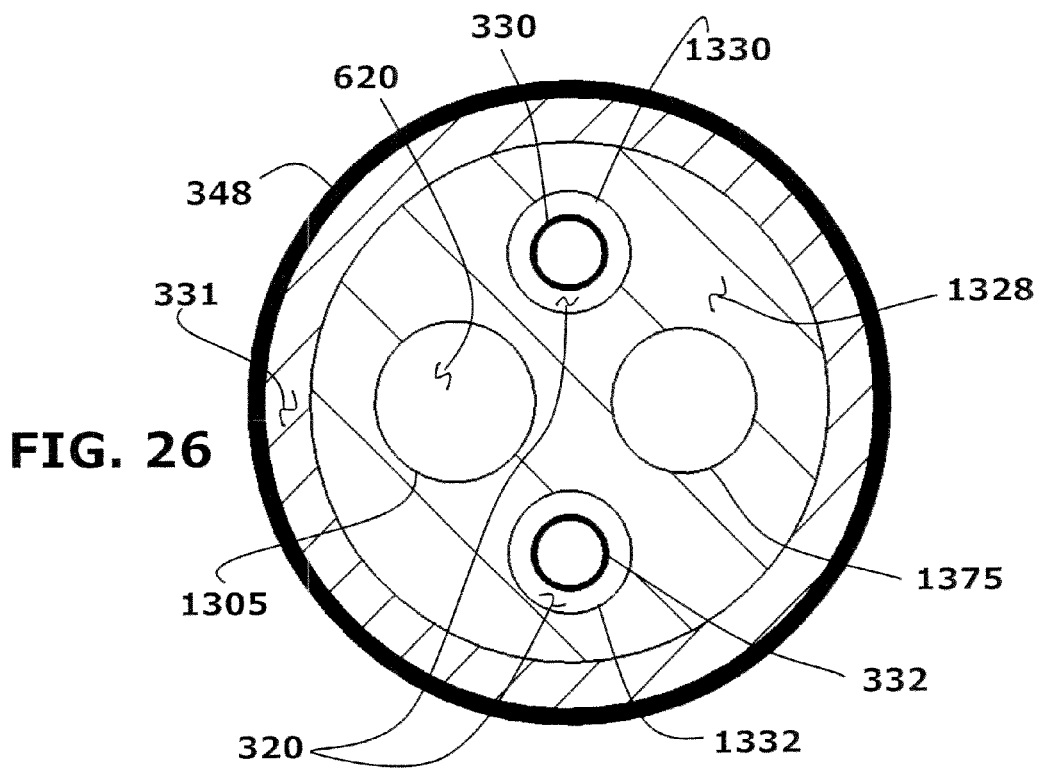
FIG. 26 is a cross-sectional view taken along line O-O in FIG. 24.

The guide wire lumen 1375 is extended on both ends by two thermally bonded short sections of the guide wire tube 375 as shown in FIGS. 19 and 24. The distal end of the balloon-fluid lumen 1305 terminates at the airtight seal 336 and is in fluid communication with the fluid chamber 620. Balloon fluid 311 travels from the fluid inlet ports 309 to the distal end of the balloon-fluid lumen 1305 through a side port 1304 (see FIG. 25). The side port 1304 is created by removing a portion of the sidewall of the outer multi-lumen 1328 that encloses the balloon-fluid lumen 1305, allowing for fluid communication between the balloon-fluid lumen 1305 and fluid inlet ports 309. A plug 1306 is positioned on the proximal-most end of the balloon-fluid lumen 1305 to prevent balloon fluid 311 from migrating into the vacuum chamber 320. This is best shown in FIGS. 24-25. In this embodiment, the balloon 303 that is normally thermally bonded to the fluid delivery tube 305 in the earlier embodiment is now bonded directly to the outer-lumen 1328.

Eliminating the fluid delivery tube 305 and using an outer lumen 1328 that essentially functions as the outer tube for the catheter body 306 allows the catheter body to be more compact, and easier to assemble. Performance is also improved due to lesser energy loss as the delivery tubes 330, 332 are separated to minimize energy transfer from one delivery line to a second delivery line/return line.

The present invention also incorporates features designed to prevent unsafe operating conditions. The catheter 102 has a vacuum chamber 320 and a fluid chamber 620. The vacuum chamber 320 is the internal volume enclosed by the tube adapter 317, an outer hose 324, a straight connector 345, a three-way connector 307, a four-way connector 331, an outer lumen 328, and among the seven airtight seals 315, 316, 346, 347, 402, 355, and 336 located at the connector section 300, the proximal section 304, and the distal section 308, respectively. In other words, the vacuum chamber 320 extends from the proximal end of the hose section 302 to an airtight seal 336 at the distal section 308. The vacuum chamber 320 is designed to enclose and insulate all internal components to minimize thermal transfer with ambient environment. Enclosing the fluid-carrying components (such as delivery tubes 330, 332, 4330, and 4332 within the vacuum chamber 320) enable leaked fluid to be captured. A pressure monitoring device can be incorporated within the cryoablation system 106 to detect any abnormal pressure level within the vacuum chamber 320. Once an abnormal pressure level is detected, a shutdown routine can be incorporated within the cryoablation system 106 to exhaust accumulated pressure from the vacuum chamber, and also to stop further fluid inflow to the catheter.

The fluid chamber 620 is another separately self-contained chamber that can be used to monitor abnormal pressure level or leakage in the catheter 102 when connected to a pressure-sensing device. In a single-lumen catheter design, the fluid chamber 620 further encloses a portion of the length of the vacuum chamber 320 from the distal section 308 to the distal end of the proximal section 304. The vacuum chamber 320 serves as secondary layer of protection against leakage out of the vacuum chamber 320. The fluid chamber 620 can capture and contain fluid leaking from the delivery tubes 332 at the distal end. Both the vacuum chamber 320 and the fluid chamber 620 can be incorporated with a pressure monitoring system for safety purpose. The pressure monitoring system can be incorporated within the cryoablation system 106.

During normal operation, the catheter 102 is introduced into the vascular structure with an outer guiding catheter and a guide wire. The outer guiding catheter leads and directs the distal end of the catheter 102 to the entrance of the ablation area of interest. The guide wire further directs the catheter 102 as it exits the outer guiding catheter and positions the distal section 308 of the catheter 102 at the desired location. The catheter 102 receives working fluid from a cryobalation system 106 which delivers cold/warm fluid to one of the inlet connectors 310, and receives the return gas from the return connector 310. The system also has the ability to create high vacuum pressure level and provision for connecting to a vacuum connector 312.

Figure 17:
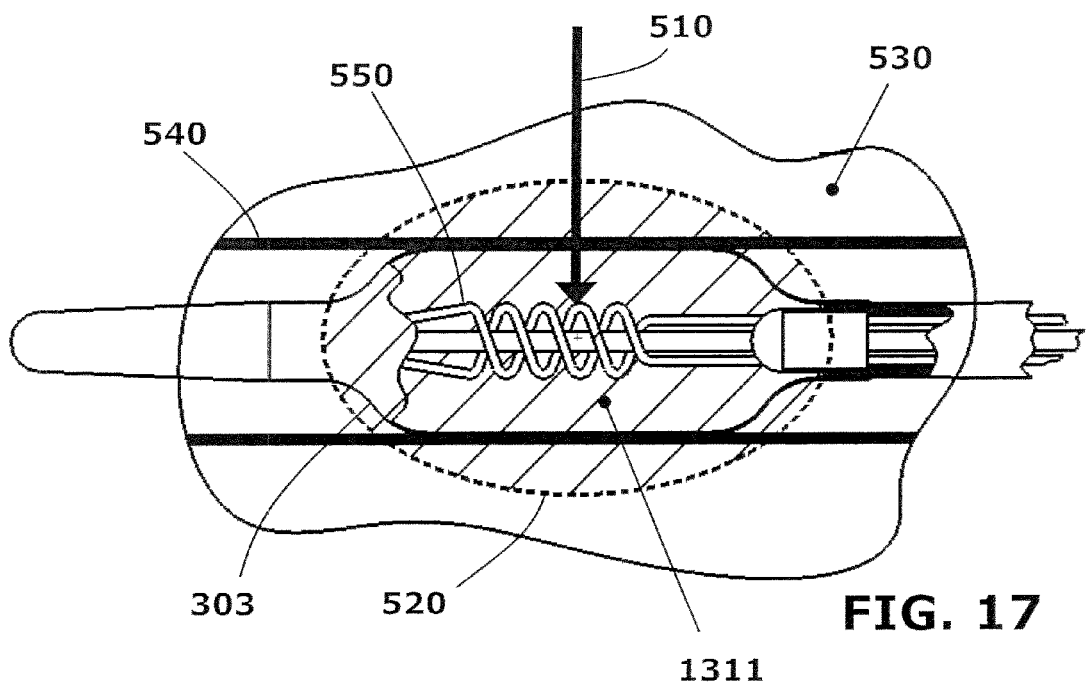
FIG. 17 illustrates the thermal transfer path during a freeze treatment cycle.

During a freeze cycle, the catheter 102 is positioned at a desired location within a blood vessel, and then the balloon 303 is inflated to contact the vessel wall 540. Once the balloon 303 is inflated, the balloon wall contacts the blood vessel wall 540, thereby occluding blood flow through the artery. The volume of blood normally surrounding the distal section 308 is taken up by the volume of balloon fluid 311 that filled the inflated balloon 303. The volume of balloon fluid 311 within the inflated balloon 303 creates a thick layer of separation between the thermal transfer element/freezing element 550 (i.e., the single-loop element 350, double coiled element 351, and the un-insulated section of delivery tubes 330 and 332) at the distal section 308 and the surrounding blood, thereby minimizing the freezing of blood. During the freeze treatment cycle, the fluid within the balloon 303 changes into solid phase up to the balloon wall, and facilitates a direct conductive path with the vessel wall 540. Body heat is removed through the balloon wall and is conducted through the ice layer within the balloon 303 to the thermal transfer element/freezing element 550 (i.e., the single-loop element 350, double coiled element 351 and un-insulated section of the delivery tubes 330 and 332 as shown in FIG. 17) at the distal section 308. As the outer balloon wall drops below freezing point, ice formation begins and grows through and beyond the vessel wall 540 forming a mechanical/ice bond with the balloon outer wall. As shown in FIG. 17, thermal transfer path 510 draws heat from the body tissue region 530 through the vessel wall 540 and through the balloon 303 and the frozen balloon fluid 1311 to the thermal transfer element 550 to be carried away from the distal section 308 during a freeze treatment cycle. The ice that forms around the distal section 308 forms an ice ball outer boundary 520 that continuously increases to an equilibrium size with time.

Figure 18:
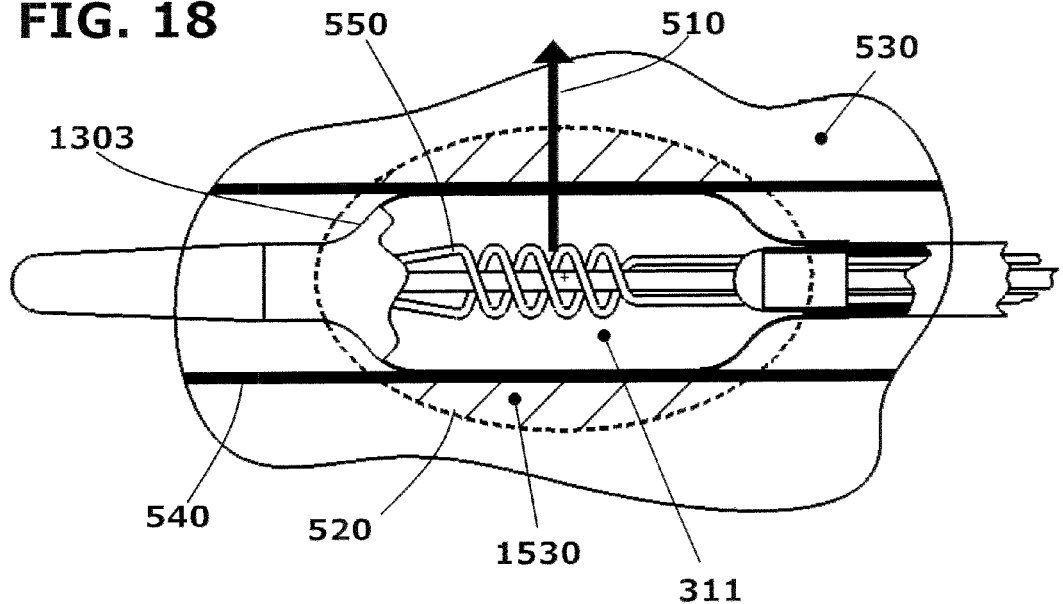
FIG. 18 illustrates the thermal transfer path during a thaw cycle.

At the end of the freeze treatment cycle, a thaw cycle needed to melt the surrounding ice in preparation for catheter retrieval. During the thaw cycle, warm nitrogen gas feeds into the catheter gas connector 310 and begins conducting warm energy to the surrounding ice at the distal section 308 through the thermal transfer element 550. Ice surrounding the distal section 308 begins to melt and changes into liquid phase. The outer balloon wall acquires heat energy through the melted ice and its temperature begins to rise above freezing point, melting away the mechanical/ice bond that holds the outer balloon wall to the vessel wall 540. The catheter removal can be accomplished after extracting the fluid within the balloon 303. As shown in FIG. 18, heat energy radiates from the thermal transfer element 550 and thaw the surrounding ice into balloon fluid 311. Heat energy further travels through the balloon wall 303, the vessel wall 540, and to the body tissue 530 to melt the surrounding ice. The temperature of surrounding tissue further increases with time, up to the maximum temperature of the delivered warm nitrogen gas. The catheter 102 can be removed even though the body tissue region 1530 is not yet thawed.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A cryoablation system, comprising:
   a gas source which provides a working nitrogen gas at room temperature and at a constant set pressure;
   a liquid generator which is coupled to the gas source to receive the working gas, and which then generates a working cryogen fluid;
   a catheter coupled to the liquid generator for receiving the working cryogen, the catheter having a catheter body that has a distal section having a freezing element which delivers the working cryogen to a treatment location, and a balloon enclosing the freezing element, wherein the catheter body has an outer tube, a first lumen positioned inside the outer tube and coaxially spaced from the outer tube to define a fluid delivery space, the first lumen having two delivery tubes and a guide wire tube positioned inside the first lumen; and wherein the freezing element includes portions of the two delivery tubes configured as a double-coiled element incorporated in series with a single-loop element, wherein the single-loop element is embedded within a flexible soft tip positioned distal of the distal section.

2. The system of claim 1, wherein the system further includes a vacuum system for providing a vacuum level to maintain proper thermal insulation to the cryogenic delivery lines against atmospheric heat.

3. The system of claim 2, wherein the fluid delivery space communicates with the interior of the balloon.

4. The system of claim 1, wherein the delivery tubes and guide wire tube are positioned parallel within the first lumen, wherein the respective tubes are separated by a vacuum space.

5. The system of claim 1, wherein the balloon is made from polyurethane, nylon, or PET.

6. The system of claim 1, wherein the freezing element is made from an annealed 70/30 Copper-Nickel alloy having an outer diameter within the range of 0.019 inches (0.508 mm) to 0.026 inches (0.660 mm) and an inner diameter of 0.015 inches (0.406 mm) to 0.020 inches (0.508 mm).

7. The system of claim 1, wherein the guide wire tube has a distal end which exits the catheter at the distal section, and a proximal end that is coupled to a connector port.

8. The system of claim 1, wherein a portion of the guide wire tube is positioned radially inside the inner diameter of the double-coiled element.

9. A cryoablation system, comprising:
 a gas source which provides a working nitrogen gas at room temperature and at a constant set pressure;
 a liquid generator which is coupled to the gas source to receive the working gas, and which then generates a working cryogen fluid;
 a catheter coupled to the liquid generator for receiving the working cryogen, the catheter having a catheter body that has a distal section having a freezing element which delivers the working cryogen to a treatment location, and a balloon enclosing the freezing element, wherein the catheter body has an outer tube, with two delivery tubes, a guide wire tube, and a fluid delivery tube positioned inside the outer tube; and
 wherein the freezing element includes portions of the two delivery tubes configured as a double-coiled element incorporated in series with a single-loop element, wherein the single-loop element is embedded within a flexible soft tip positioned distal of the distal section.

10. The system of claim 9, wherein the guide wire tube has a distal end which exits the catheter at the distal section, and a proximal end that is coupled to a connector port.

11. The system of claim 9, wherein the delivery tubes are positioned parallel with each other within the outer tube, and spaced apart from the guide wire tube and the fluid delivery tube, with the space between the respective tubes filled by a solid material.

12. The system of claim 9, wherein the outer tube has four integral circular cavities along the entire length, wherein the cavities are arranged symmetrically about the centerlines of a cross-section along the length of the outer tube, wherein the delivery tubes are contained within two opposing cavities.

13. The system of claim 12, wherein the delivery tubes are separated from the inner wall cavities of the outer tube by a vacuum space.

14. A cryoablation catheter, comprising:
 a catheter body having a distal section that has a freezing element which delivers working cryogen to a treatment location;
 a balloon provided at the distal section and enclosing the freezing element;
 a flexible soft tip positioned distal of the distal section to define a distal end of the catheter body;
 wherein the catheter body has an outer tube, with two delivery tubes, a guide wire tube, and a fluid delivery tube provided integrally within the outer tube, with the guide wire tube positioned concentrically with respect to both the freezing element and the flexible soft tip, wherein a portion of the length of the guide wire tube is embedded within the flexible soft tip, with a guide wire exit port positioned at the distal end of the flexible soft tip; and
 wherein the freezing element includes portions of the two delivery tubes configured as a double-coiled element incorporated in series with a single-loop element, wherein the single-loop element is embedded within the flexible soft tip.

15. The catheter of claim 14, wherein the outer tube has an inner wall, and the delivery tubes are separated from the inner wall of the outer tube by a vacuum space.

16. The catheter of claim 14, wherein the guide wire tube is a straight tube having a distal end that exits the catheter body and the flexible soft tip at the distal end of the flexible soft tip, and a proximal end that is coupled to a connector port.

* * * * *